United States Patent [19]

Child et al.

[11] Patent Number: 5,196,626
[45] Date of Patent: Mar. 23, 1993

[54] FILM TYPE ALKYLATION PROCESS

[75] Inventors: Jonathan E. Child; Tomas R. Melli, both of Sewell, N.J.

[73] Assignee: Mobil Oil Corporation, Fairfax, Va.

[21] Appl. No.: 787,185

[22] Filed: Nov. 4, 1991

[51] Int. Cl.$^5$ ............................................. C07C 2/62
[52] U.S. Cl. .................................... 585/720; 585/723; 585/709
[58] Field of Search ............... 585/709, 720, 730, 731

[56] References Cited

U.S. PATENT DOCUMENTS

| | | | |
|---|---|---|---|
| 2,380,234 | 7/1945 | Hall | 260/683.4 |
| 2,855,449 | 10/1958 | Owen | 585/720 |
| 2,995,612 | 8/1961 | Hervert | 585/720 |
| 3,133,128 | 5/1964 | McDonald | 585/720 |
| 3,456,033 | 7/1969 | Borst, Jr. | 260/683 |
| 3,469,949 | 9/1969 | Borst, Jr. | 23/285 |
| 3,501,538 | 3/1970 | Archer et al. | 260/652 |
| 3,780,130 | 12/1973 | Miller | 260/683 |
| 3,817,708 | 6/1974 | Vernon | 23/260 |
| 3,914,110 | 10/1975 | Anderson | 23/288 |
| 4,000,212 | 12/1976 | Chapman | 585/720 |
| 4,769,511 | 9/1988 | O'Neil | 585/719 |
| 4,783,567 | 11/1988 | Kocal | 585/464 |
| 4,891,466 | 1/1990 | Kocal | 585/464 |
| 4,938,935 | 7/1990 | Audeh et al. | 423/240 |
| 4,938,936 | 7/1990 | Yan | 423/240 |
| 4,985,220 | 1/1991 | Audeh et al. | 423/240 |

OTHER PUBLICATIONS

"Alkylation of Isobutane with C$_4$ Olefins", L. F. Albright, 1988, pp. 382-386.

"Alkylation Will Be Key Process in Reformulated Gasoline Era", L. F. Albright Oil & Gas Journal, Nov. 12, 1990, pp. 79-92.

"H$_2$SO$_4$, HF Processes Compared, And New Technologies Revealed", L. F. Albright Oil & Gas Journal, Nov. 26, 1990, pp. 70-77.

*Handbook of Petroleum Refining Processes*, R. A. Meyers, 1986, pp. 23-28.

"Sulfuric Acid Alkylation Process in Film Reactor", I. Pervez', C. Karagiozov & C. Boyadjiev, Chemical Engineering Science, vol. 46, No. 7, pp. 1589-1594, 1991.

*Primary Examiner*—Anthony McFarlane
*Attorney, Agent, or Firm*—Alexander J. McKillop; Dennis P. Santini; Robert B. Furr, Jr.

[57] ABSTRACT

The present invention includes an isoparaffin:olefin alkylation process and apparatus in which liquid acid inventory is reduced and temperature control is improved by reacting the isoparaffin:olefin feed with a thin film of liquid acid catalyst supported on a heat exchange surface.

12 Claims, 2 Drawing Sheets

FILM TYPE ALKYLATION PROCESS

FIELD OF THE INVENTION

The present invention relates to the art of catalytic alkylation. The invention relates to a liquid alkylation catalyst and an isoparaffin:olefin alkylation process Particularly, the invention provides an isoparaffin:olefin alkylation process in which the required inventory of liquid acid alkylation catalyst is markedly reduced in comparison with the current commercial technology which utilizes large quantities of liquid Bronsted acids such as sulfuric and hydrofluoric acid.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used large volumes of liquid Bronsted acid catalysts such as hydrofluoric or sulfuric acid under relatively low temperature conditions. Acid strength is preferably maintained at 88 to 94 weight percent by the continuous addition of fresh acid and the continuous withdrawal of spent acid.

Bronsted acid catalyzed isoparaffin:olefin alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

Researchers in the field have addressed the safety and environmental concerns surrounding the use of Bronsted acids in various ways, including methods for containing and/or neutralizing acid clouds following accidental releases. See, for example, U.S. Pat. Nos. 4,938,935 and 4,985,220 to Audeh and Greco, as well as U.S. Pat. No. 4,938,936 to Yan.

The two-part article, "Modern Alkylation", by Lyle F. Albright, *Oil and Gas Journal*, Nov. 12 and 26, 1990, summarizes the state of the art in alkylation technology, and highlights problems associated with liquid Bronsted acid catalysts such as HF and $H_2SO_4$, and notes safety and environmental concerns associated with using and storing substantial quantities of these acids, which concerns underscore the desirability of developing a commercially viable low acid inventory isoparaffin:olefin alkylation process.

Conventionally, hydrocarbon reactants are bubbled through a vessel (HF alkylation) or vigorously stirred with the acid to assure adequate contact between the acid and the hydrocarbon reactants (e.g., $H_2SO_4$ alkylation in a Stratco brand horizontal impelled reactor/heat exchanger). Various techniques have been explored for improving contact between a Bronsted acid catalyst and hydrocarbon reactants. For example, U.S. Pat. No. 3,780,130 describes a gas-fog alkylation process, wherein a fog or mist of acid is allowed to react with the hydrocarbon. Although this prior art noted some improvement in the alkylation process, very high voltages (up to 4000 v) are required for the generation of acid fog making the process impractical on a commercial scale.

In the process described in U.S. Pat. No. 2,380,234, a small amount of solid is dispersed in the acid phase. The resultant system shows limited improvement in the alkylation efficiency as shown by a slight increase in the alkylate yield.

More recently, U.S. Pat. No. 4,783,567, teaches a process wherein the hydrocarbon feed is contacted with hydrofluoric acid in a reactor with a fixed bed of a solid packing. The reference reported minor improvements associated with the use of solid packings.

Researchers seeking to improve reaction temperature uniformity and reactant/catalyst contact efficiency in liquid acid-catalyzed alkylation processes have developed improved reactor configurations to achieve these objectives, as shown by the following references.

U.S. Pat. No. 3,456,033 to Borst, Jr. relates to an alkylation process wherein reactant hydrocarbons and acid catalyst flow through a plurality of heat exchange tubes while a gaseous heat exchange medium passes across the tubes to remove heat of reaction.

U.S Pat. Nos. 3,469,949 and 3,501,538 to Borst, Jr. disclose a process and apparatus for carrying out an alkylation reaction which jets the hydrocarbon reactants into an upwardly flowing stream of hydrogen fluoride catalyst to impart a spiral flow path to the hydrocarbon reactants.

U.S. Pat. No. 3,817,708 to Vernon teaches an apparatus for an alkylation process, which apparatus comprises a pair of interconnected u-tube heat exchangers. The disclosed configuration is said to increase the capacity of a conventional liquid acid alkylation process.

U.S. Pat. No. 3,914,110 to Anderson teaches an alkylation reaction cooler comprising a heat exchanger, a plurality of baffles and a plurality of spray nozzles assemblies within a horizontal elongated chamber. Alkylation reactants are sprayed into the acid catalyst which flows through the elongated horizontal chamber in a serpentine flow path.

U.S. Pat. Nos. 4,783,567 and 4,891,466 to Kocal disclose alkylation processes in a vertical fixed bed which is said to improve process efficiency.

Years of industrial experience have proven that liquid Bronsted acid alkylation catalysts such as HF and $H_2SO_4$ can be handled safely. To assure continued compliance with increasingly stringent regulations governing the handling and storage of potentially hazardous materials, research efforts have now been directed toward reducing the required inventory of liquid acid catalyst in industrial isoparaffin:olefin alkylation units.

SUMMARY OF THE INVENTION

This invention provides a thin-film isoparaffin:olefin alkylation process and apparatus which not only reduce the required liquid acid inventory, but also improve temperature uniformity within the alkylation reaction zone, facilitate acid/hydrocarbon separation and acid recycle, and eliminate the necessity for mechanical mixing of the liquid acid catalyst and the hydrocarbon reactants.

The invention enhances contact between the liquid acid catalyst and the hydrocarbon reactants by maintaining the liquid acid catalyst in a thin film in direct contact with a first side of a support surface. The support surface also functions as a heat transfer surface, because a heat transfer fluid is circulated on the opposite (second) side of the surface to provide improved temperature uniformity during the exothermic alkylation reaction. Temperature excursions promote the formation of higher molecular weight conjunct polymers, commonly referred to in the industry as "acid soluble oil", or ASO. These polymers are detrimental for at least two reasons. First, their formation diverts useful reactants away from the desired alkylate product. Second, as implied by the name "acid soluble oil", these polymeric products are difficult to separate from the acid catalyst.

The invention further advances the state of the isoparaffin:olefin alkylation art by both eliminating mixing energy input to the process as well as facilitating separation of the reactor effluent hydrocarbons from the acid catalyst. In industrial isoparaffin:olefin alkylation, the acid catalyst as well as unreacted isoparaffin is separated from the alkylated product and recycled to the reaction zone. Conventional liquid acid catalyzed processes contact finely divided droplets of hydrocarbon feed (the discontinuous phase) with the liquid acid catalyst (the continuous phase). Mixing energy is required to disperse the finely divided hydrocarbon droplets into the continuous liquid acid phase.

In a first embodiment of the invention, the benefits of the thin-film reaction regime of the present invention extend further to the acid/hydrocarbon separation step. After the mixture of liquid acid and hydrocarbon flows out of a conventional isoparaffin:olefin alkylation reactor, the fine droplets of hydrocarbon must be separated from the liquid acid. But in contrast, the first embodiment of the present invention operates with two continuous phases, requiring neither mixing energy to divide the hydrocarbon feed into droplets, nor excessive residence time to gravitationally separate the mixture. Because the reaction proceeds while the acid and hydrocarbon are in two distinct phases, gravitation separation downstream from the reaction zone is markedly enhanced and the settling residence time is decreased accordingly.

In a second embodiment, the liquid film flows upwardly along the reactor wall to a predetermined point where the film is broken and separated from the reactor wall. This second embodiment compromises ease of product/catalyst separation by dispersing the acid into the hydrocarbon reactants, but improves conversion and yield by increasing contact between the reactants and the catalyst.

In the second embodiment, it is preferable to encase the lower section of the reactor in a cooling jacket to assure isothermal conditions as the reaction proceeds in the thin film regime. The lower reactor section should be sized to react a substantial portion of the olefin feed, preferably at least about 70% of the olefin feed under substantially isothermal conditions, before the acid film is broken and dispersed into the hydrocarbon phase in the upper section of the reactor.

The invention includes both method and apparatus aspects, as further set forth below.

The invention comprises, in a first method aspect, a process for alkylating an isoparaffin with an olefin comprising the steps of:

(a) providing a cylindrical alkylation reactor;

(b) providing a liquid acid catalyst distributor in said alkylation reactor;

(c) charging a liquid acid catalyst through said distributor to said alkylation reactor under controlled flow conditions including linear fluid velocities within said alkylation reaction conduit sufficient to maintain a film of liquid acid on the inner surface of said alkylation reactor;

(d) flowing a hydrocarbon mixture containing at least one isoparaffin having from about 4 to about 12 carbon atoms and at least one olefin having from about 3 to about 10 carbon atoms to said alkylation reactor; and (e) effecting reaction of isoparaffin and olefin with said film of liquid acid catalyst wherein alkylation conditions include temperature from about −40° to about 500° C. and pressure from subatmospheric to about 5000 psig.

The invention further provides, in a second method aspect, a process for alkylating an isoparaffin with an olefin comprising the steps of:

(a) providing a cylindrical alkylation reactor;

(b) providing a liquid acid catalyst distributor in said alkylation reactor;

(c) charging a liquid acid catalyst through said distributor to said alkylation reactor under controlled flow conditions including linear fluid velocities within said alkylation reaction conduit sufficient to maintain a film of liquid acid on the inner surface of a lower portion of said alkylation reactor;

(d) flowing a hydrocarbon mixture containing at least one isoparaffin having from about 4 to about 12 carbon atoms and at least one olefin having from about 3 to about 10 carbon atoms to said alkylation reactor;

(e) effecting reaction of isoparaffin and olefin with said film of liquid acid catalyst in said lower portion of said alkylation reaction conduit wherein alkylation conditions include temperature from about −40° to about 500° C. and pressure from subatmospheric to about 5000 psig;

(f) breaking said film of liquid acid and dispersing said liquid acid into said hydrocarbon mixture.

In an apparatus aspect, the invention includes a reactor comprising:

(a) an alkylation reaction zone having a support surface with a first side for retaining a film of liquid acid alkylation catalyst and a second side for contacting a heat transfer fluid;

(b) an acid flow distributor for passing a liquid acid catalyst onto said first side of said support surface in a flow regime to maintain a substantially continuous film of liquid acid catalyst on said first side of support surface;

(c) conduit for introducing reactants into said alkylation reaction zone in substantially laminar contact with said liquid acid catalyst film; and (d) heat exchange conduit for flowing a heat transfer fluid in contact with said second side of said support surface to withdraw heat from said liquid acid catalyst film.

DETAILED DESCRIPTION

Figure 1:
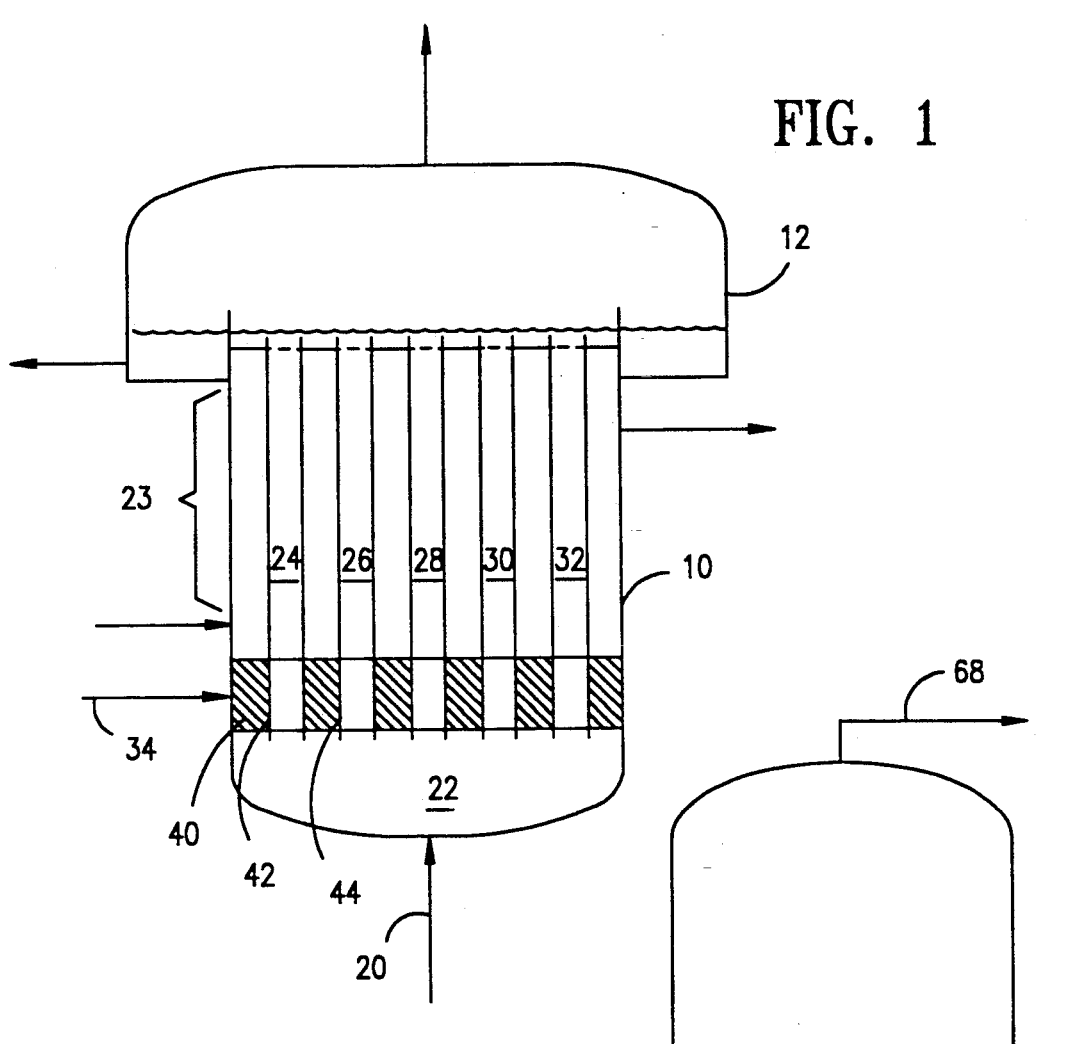
FIG. 1 is a simplified schematic diagram of a first embodiment of the apparatus of the invention.

The present invention reduces the required liquid acid catalyst inventory for industrial isoparaffin:olefin alkylation while maintaining the necessary conversion and yield required for economic operation.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference as if set forth at length herein.

The molar ratio of isoparaffin to olefin is generally from about 1:1 to about 100:1, preferably from about 1:1 to about 50:1, and more preferably from about 5:1 to about 10:1.

Bronsted Acids

Bronsted acids suitable for use in the present invention are characterized by very high acidity sufficient to catalyze isoparaffin:olefin alkylation. Those Bronsted acids which find utility in the present invention are also present in the liquid state under the conditions at which the alkylation reaction is suitably conducted. Examples of liquid Bronsted acids useful in the present invention include trifluoromethanesulfonic acid ($CF_3SO_3H$), fluorosulfonic acid ($HSO_3F$), sulfuric acid ($H_2SO_4$) and hydrofluoric acid (HF).

Process Conditions

The present alkylation process is suitably conducted at temperatures of from about $-40°$ to about 500° C., preferably from about $-40°$ to about 200° C., and more preferably below about 150° C. to avoid undesirable side reactions. Lower reaction temperatures are preferred to maximize alkylate octane. The upper temperature limit is more critical to avoid undesirable side reactions. Lower temperatures are generally preferred, for example temperatures as low as $-20°$ C. may be effectively employed. Operating temperature typically falls within the range of about 0° to about 40° C.

Operating pressure is controlled to maintain the reactants in the liquid phase, and is suitably from about 50 to about 1500 psig, preferably from about 100 to about 500 psig. The catalyst weight hourly space velocity as well as the Bronsted acid dosage varies with the particular combination of feedstream composition, Bronsted acid, and any additives which may be admixed with the selected Bronsted acid.

Hydrocarbon and catalyst flow through the alkylation zone is typically controlled to provide weight hourly space velocity (WHSV) sufficient to convert about 99 percent by weight of fresh olefin to alkylate product. Typical WHSV values typically fall within the range of from about 0.01 to about 10 $hr^{-1}$.

The particular operating conditions used in the present process will depend on the specific alkylation reaction being effected. Process conditions such as temperature, pressure, space velocity and molar ratio of the reactants will effect the characteristics of the resulting alkylate, and may be adjusted within the disclosed ranges by those skilled in the art with only minimal trial and error.

Process Flow

A first embodiment of the process of the invention is described below with reference to FIG. 1.

The process of the invention is suitably conducted in a vertical cylindrical reactor vessel 10, which is preferably swaged to provide a larger diameter upper portion 12 for decantation of liquid acid catalyst from hydrocarbon. Mixed hydrocarbon charge containing olefin and excess isoparaffin flows through line 20 and enters a feed distribution zone 22 near the bottom. The configuration and relative volume of the feed distribution zone is not a critical aspect of the inventive process, but is an important operational aspect to the extent that hydrocarbon flow is evenly distributed among the reaction conduits. Further, while reactor vessel substantially resembling a vertical shell-and-tube heat exchange is illustrated in FIG. 1, it is to be understood that such illustration is not limiting, and that other suitable reactor configurations may be employed, which include but are not limited to plate-and-frame heat exchangers.

The hydrocarbon reactant mixture containing olefin and excess isoparaffin then flows upwardly into a plurality of substantially vertical conduits 24, 26, 28, 30, and 32 (only five are designated) extending from said lower acid catalyst distribution zone, through a central heat exchange zone designated generally as 23, and into said upper gravitational separation zone contained in the larger diameter upper portion 12 of the reactor vessel 10. While the substantially vertical conduits may be of any suitable cross-sectional shape and wall thickness, the conduits are typically cylindrical with relatively thin walls, and are referred to hereinafter as tubes. The tubes may optionally be fluted or ridged to increase their surface area and to promote the formation of a thin film of liquid acid catalyst as is described in greater detail below.

Each tube includes an acid flow distributor located in the lower portion of the tube wall which extends through the acid distribution zone 40. The purpose of the acid flow distributors is to allow the liquid acid catalyst to flow from the acid distribution zone into each of the tubes such that the acid catalyst readily adheres to the inner face of the tube wall to form a thin film of acid catalyst. Flowing the liquid acid through the tubes in a thin film flow regime is an important, and even critical aspect of the present invention.

Liquid acid catalyst enters the acid distribution zone 40 through line 34 and enters the tubes 24, 26, 28, 30, and 32 through acid flow distributors in each tube wall. Acid flow distributors located in the walls of tubes 24 and 26 are designated as 42 and 44 (only two acid flow distributors are designated).

Figure 2:
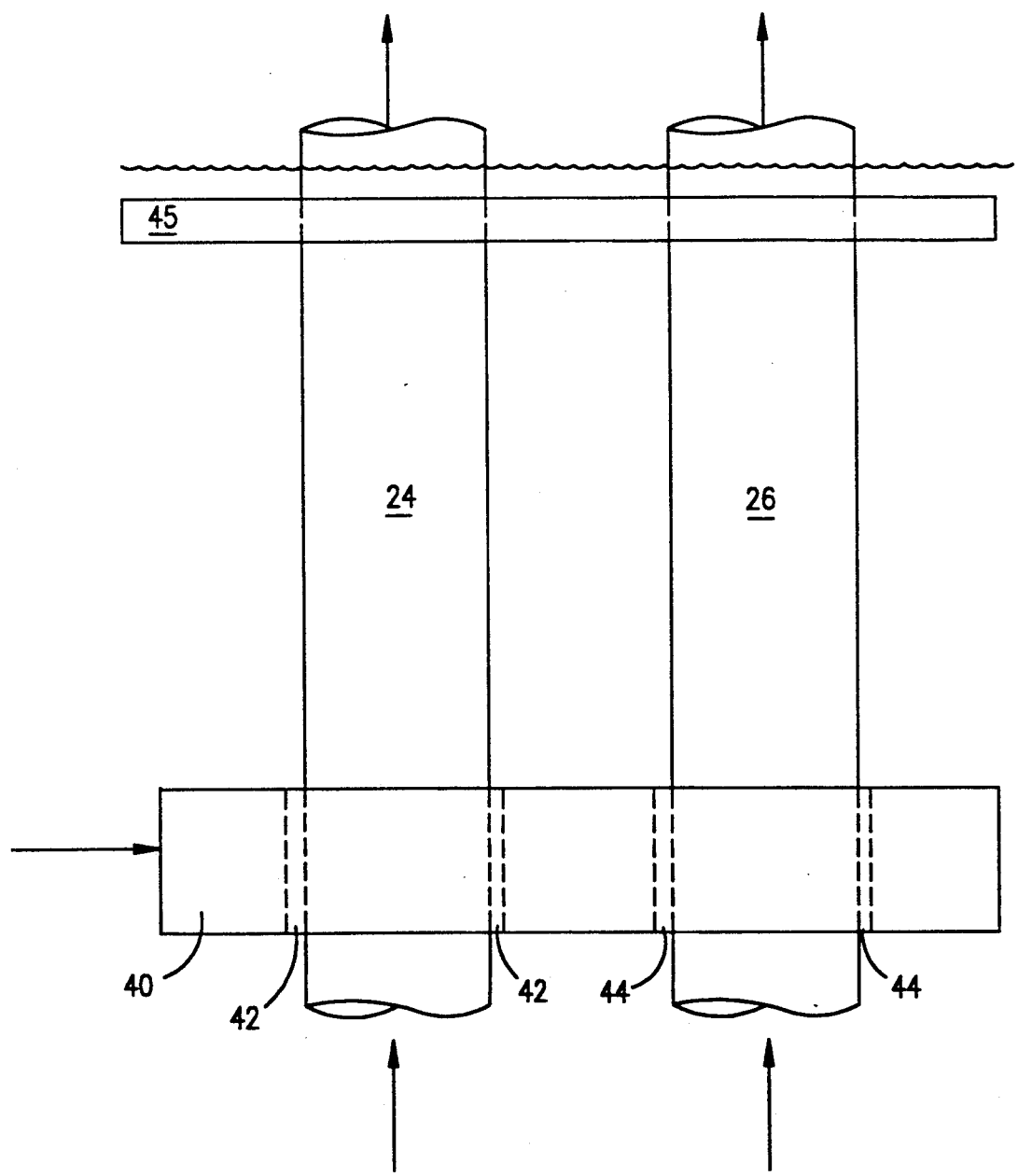
FIG. 2 is a simplified schematic diagram illustrating liquid acid distribution and separation features of a first embodiment of the invention.

Referring now to FIG. 2, the acid distribution zone 40 is shown with tubes 24 and 26. The section of tube 24 which passes through acid distribution zone 40 contains a porous wall section designated as 42. Other acid distributors may also be used, for example narrow slits, or closely fitting concentric conduits. If a porous wall section is used, however, the acid must flow from the pores of the acid distribution zone at less than jetting velocity, and preferably flows from the pores at or below droplet forming velocity. Thus the acid typically flows through the pores of the acid distribution zone at linear velocities of less than about 0.1 meter per second.

The acid distributor preferably comprises an acid-resistant sintered metal, for example a sintered Monel or Hastelloy alloy. Sintered ceramics, such as sintered siliceous materials, are generally not preferred due to their reactivity with HF.

Figure 3:
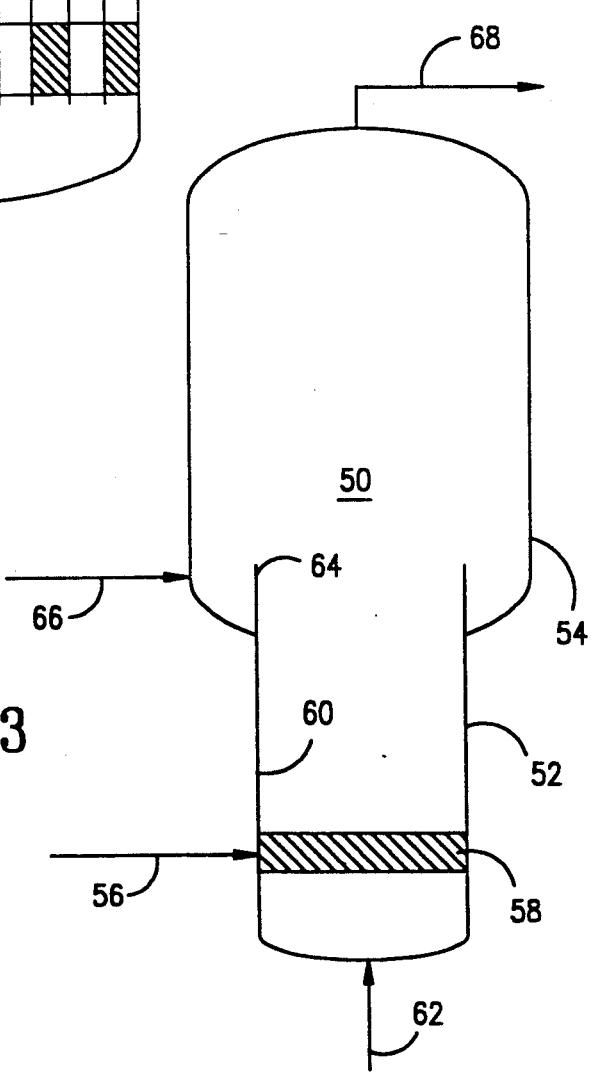
FIG. 3 is a simplified schematic diagram illustrating a second embodiment of the apparatus of the invention.

FIG. 3 illustrates a suitable apparatus for conducting a second embodiment of the process of the invention. The reactor 50 comprises a smaller diameter lower section 52 and a larger diameter upper section 54. Acid catalyst enters the lower section 52 through inlet line 56 and distributor 58. The distributor 58 may be any suitable device for flowing the acid onto the inner surface of the lower section 52, although acid-resistant sintered metal is preferred. The acid flows upwardly, forming a film 60 which is maintained by controlling the relative flowrates of the hydrocarbon reactants (from line 62) and the acid catalyst.

When the acid film reaches the upper edge 64 of lower section 52, the acid film 60 flows off of the inner surface of the cylindrical wall and is dispersed into the upwardly flowing hydrocarbon mixture. An additional stream of hydrocarbon reactants, containing isoparaffin, or both isoparaffin and olefin, may optionally be injected through line 66 at a level near the upper edge 64 of lower section 52 to improve dispersion of the acid into the hydrocarbon phase. Reactor effluent (containing acid, unreacted isoparaffin, and alkylate product) flows out of reactor 50 through line 68 for further processing and storage.

Lower section 52 of reactor 50 is preferably surrounded by a cooling jacket (not shown) for circulating water (or other cooling medium) in contact with the outer surface of the lower section 52.

Thin Film Liquid Acid Flow Regime

The minimum acid charge rate for the process is controlled by the minimum film thickness required to maintain a substantially continuous liquid film. The acid film is preferably as thin as possible consistent with maintaining a continuous film on the inner surface of the reactor wall. The acid preferably flows onto the inner surface of the reactor wall through a sintered metal distributor. The velocity of acid flowing through the openings in the sintered metal distributor must be below jetting velocity, and is preferably at or below droplet forming velocity. Suitable acid velocities through the openings in the sintered metal distributor typically fall below about 0.1 meter per second.

The minimum acid charge rate is determined by the required film thickness to maintain a continuous film. While the acid thickness continuously varies during operation due to the interactions (e.g., eddies) at the wall/acid interface and the acid/hydrocarbon interface, the variation in acid film thickness should be less than the nominal thickness of the film to assure a continuous film.

Hydrocarbon reactants flowing upwardly (in contact with the acid film) drag the film up the walls of the reaction zone. To assure that the acid flows upwardly, the hydrocarbon phase velocity is typically maintained above about 0.15 meter per second (0.5 feet per second), preferably above about 0.30 meter per second (1.0 feet per second). Alkylate product quality determines the maximum hydrocarbon charge rate. The total hydrocarbon charge rate (in units of meters$^3$/second) is typically less than the product of the area of the hydrocarbon:acid film interface (in units of meters$^2$) divided by 15,000.

EXAMPLES

This is an example of the first embodiment of the invention as described above.

| | |
|---|---|
| Production Capacity: | 2000 barrels per stream day |
| Total Hydrocarbon Feedrate: | 130 m$^3$/hr (572 gal/min) |
| Isoparaffin: olefin mole ratio: | 15 |
| Acid: total hydrocarbon volume ratio: | 0.3 |
| Dimensions: | |
| Tubes, OD | 3/8 in (0.95 cm) |
| Number of tubes | 2600 |
| Tube length | 23 ft (7 m) |
| Shell I.D. | 45 in (114.3 cm) |
| Number of passes | 4 |
| Pitch | 13/16 in (2.06 cm) |
| Residence time: | 16 sec |
| Heat exchange area: | 2.9 ft$^2$/bbl alkylate |
| Acid film thickness: | 0.7 mm (0.028 in) |
| Acid flow rate: | 39 m$^3$/hr (171.68 gal/min) |
| Operating pressure: | 1030–1380 kPa (150–200 psia) |
| Operating temperature: | 32° C. (90° F.) |

Changes and modifications in the specifically described embodiments can be carried out without departing from the scope of the invention which is intended to be limited only by the scope of the appended claims.

What is claimed is:

1. A process for alkylating an isoparaffin with an olefin comprising the steps of:
   (a) providing a cylindrical alkylation reactor;
   (b) providing a liquid acid catalyst distributor in said alkylation reactor;
   (c) charging a liquid acid catalyst through said distributor to said alkylation reactor under controlled flow conditions including linear fluid velocities within said alkylation reactor sufficient to maintain a film of liquid acid flowing upwardly on the inner surface of said alkylation reactor;
   (d) flowing a hydrocarbon mixture containing at least one isoparaffin having from about 4 to about 12 carbon atoms and at least one olefin having from about 3 to about 10 carbon atoms upwardly through said alkylation reactor;
   (e) effecting reaction of isoparaffin and olefin with said film of liquid acid catalyst wherein alkylation conditions include temperature from about −40° to 500° C. and pressure from subatmospheric to about 5000 psig; and
   (f) breaking said liquid film and dispersing said liquid film into said hydrocarbon.

2. The process of claim 1 further comprising breaking said liquid film at the height of said reactor corresponding to conversion of about 70 weight percent of the olefin feed.

3. The process of claim 1 wherein said liquid film breaking step further comprises dispersing said liquid film into finely divided droplets.

4. The process of claim 1 wherein said liquid film breaking step further comprises flowing said liquid film in contact with vanes facing inwardly with respect to the center of said alkylation reactor.

5. The process of claim 1 wherein said liquid film breaking step further comprises flowing said liquid film and said hydrocarbon into a second, larger, cylindrical reactor which is substantially concentric with said reactor of step (a).

6. The process of claim 1 further comprising controlling hydrocarbon residence time within said reactor to convert substantially all of said olefin to alkylate product.

7. The process of claim 1 further comprising introducing acid into said alkylation reactor through the open area of a porous surface to form said liquid film.

8. The process of claim 7 wherein said acid exits said pores at less than jetting velocity.

9. The process of claim 8 wherein said acid exits said pores at velocity of less than about 0.1 meter per second.

10. The process of claim 1 further comprising flowing said hydrocarbon mixture and said liquid acid catalyst cocurrently through said alkylation reactor.

11. The process of claim 1 further comprising charging said liquid acid from a liquid acid distribution header to said alkylation reactor through a porous wall portion of said alkylation reactor.

12. The process of claim 1 further comprising flowing hydrocarbon and liquid acid catalyst from an upper portion of said alkylation reactor to a decantation zone, which decantation zone is located above and substantially concentric with said alkylation reactor.

* * * * *